United States Patent [19]
Hodgen et al.

[11] Patent Number: 5,681,817
[45] Date of Patent: Oct. 28, 1997

[54] TREATMENT OF OVARIAN ESTROGEN DEPENDENT CONDITIONS

[75] Inventors: Gary D. Hodgen; Robert F. Williams, both of Norfolk, Va.; Daniel Grow, Longmeadow, Mass.

[73] Assignee: The Medical College of Hampton Roads, Norfolk, Va.

[21] Appl. No.: 191,631

[22] Filed: Feb. 4, 1994

[51] Int. Cl.$^6$ .......................... A61K 38/00; A61K 35/48; A61K 38/24; C07K 14/59

[52] U.S. Cl. ................... 514/12; 514/9.1; 514/21

[58] Field of Search .................. 514/12, 21, 9.1

[56] References Cited

PUBLICATIONS

Terakawa, N., "Studies on Endocrive Therapy for Endometriosis", Acta ohstet. Gynaecol. JPN (JPN ED) 41 (8) pp. 981–989 (1989). (Abstract).

Garzo et al., "Effects of antiprogesterone (RD486) . . . Cycle", J. Clin. Eud. Metah., 66(3), 508–17 (1988).

Carr et al., "An Evaluation . . . , Crossover Trial,", J. Clin. Endocrinology, vol. 76, No. 5, pp 1217–1223 (1993).

Primary Examiner—Cecilia J. Tsang
Assistant Examiner—P. Lynn Touzeau
Attorney, Agent, or Firm—Ostrolenk, Faber, Gerb & Soffen, LLP

[57] ABSTRACT

A method of treating an ovarian estrogen dependent condition such as endometriosis, uterine leiomyomata, PMS or DUB involving the administration of gonadotropin releasing hormone analog and the administration of antiprogestin, which will provide a therapeutic method for long term treatment without rapid loss of bone density, as occurs using GnRH analogs alone.

16 Claims, 3 Drawing Sheets

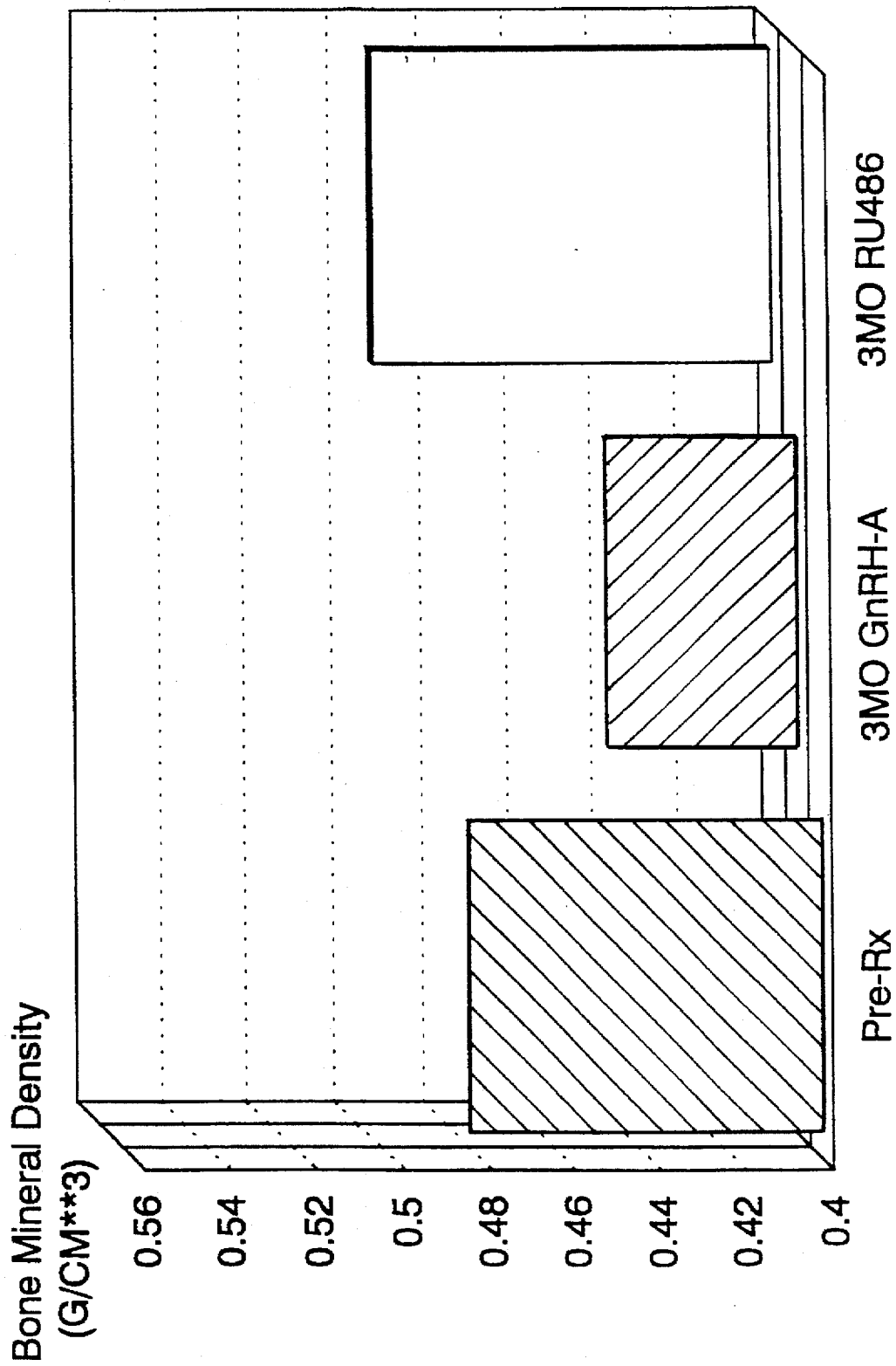

TREATMENT OF OVARIAN ESTROGEN DEPENDENT CONDITIONS

BACKGROUND OF THE INVENTION

Endometriosis is the ectopic presence of endometrial type glands and stroma in sites which are outside of the uterus. This ectopic occurrence of endometrial tissue frequently forms cysts containing altered blood. The condition results in debilitating pain for millions of women worldwide and particularly occurs in conjunction with the monthly proliferation of endometrial tissue. Endometriosis is frequently a lifelong condition.

Endometriosis can be treated by a variety of medical therapies but none of these are sufficiently effective for a long term treatment beyond six months or more. Perhaps the oldest therapy with a demonstrable effect is the administration of progestin either by injection, orally or in combination with oral contraceptives. However, long term administration of progestins, especially androgenic ones, have been associated with a number of undesirable side effects and has not received regulatory approval in the United States.

A synthetic steroid derived from ethisterone, namely 17-α-pregna-2,4-dien-20-yno[2,3-d]-isoxazol-17-ol, also known as danazol and marketed under the trademark Danocrine has been shown an effective medication for the treatment of endometriosis producing a hypoestrogenic milieu. Unfortunately, this drug also has many androgenic side effects. In addition to the vasomotor flush of estrogen depravation, it causes weight gain, long muscle cramps, breast atrophy, hot flashes, mood swings, oily skin, depression, edema, acne, fatigue, hirsutism, alterations in the libido, headache, rash and a deepening of the voice.

One of the most effective treatments of endometriosis is the administration of a gonadotropin releasing hormone agonist which suppresses pituitary gonadotropin secretion and therefore induces a state of reversible pseudomenopause. Although individual response varies, endometriosis usually quickly regresses within only three months of initiation of therapy. On withdrawal of the treatment, pain often returns and the endometriosis reappears several months after the return of normal menstrual cycles. The drug can also be used to treat uterine fibroid tumors (leiomyomata). The main drawback of this therapy is a series of side effects stemming from protracted severe hypoestrogenism or the pseudo-menopausal state induced by severe estrogen deprivation, namely hot flashes, bone loss and loss of cardiovascular protection by estrogen. Indeed, the object of hormone replacement therapy is to provide estrogen and/or progestin and thereby prevent bone loss. While individual response again varies, the bone loss generally begins to be measurable after about 3 months of therapy and becomes highly significant after about 6 months of therapy in the most vulnerable patients. The total unacceptability of this side effect from a risk-benefit point of view is apparent from the fact that the mortality index is about 3.2 years after a post-menopausal woman experiences a break of the hip bones due to osteoporosis. Because of this side effect, the United States Food & Drug Administration prohibits any administration of a gonadotropin releasing hormone analog after six months of total administration has elapsed. In other words, the drug cannot be readministered after a resting period according to FDA labelling requirement.

Leiomyomata and endometriosis share ovarian estrogen dependency. A drug which has been noted to have efficacy in the treatment of endometriosis and uterine leiomyomata is antiprogestin (sometimes termed "progesterone antagonists" or "anti-gestagens"). See, e.g., Chwalisz et al., *Endocrinology*, 129(1):312, 1991; Kettel et al., *Fertil Steril*, 56(3):402, 1991; Murphy et al., *J. Clin. Endocrinol. Metab.*, 76(2):513, 1993. See also Gravanis et al., *J. Clin. Endocrinol. Metab.*, 60:156, 1986 and Wolf et al., *Fertil Steril*, 52:1055, 1989.

Premenstrual syndrome (PMS) and dysfunctional uterine bleeding (DUB) are also conditions which share a common cyclic hormonal requirement derived from the estrogen production of the ovaries.

Studies have been made on the use of a combination of a gonadotropin releasing hormone agonist (leuprolide) and progestin (medoxyprogesterone acetate) in the treatment of uterine leiomyomata. With concomitant treatment, the progestin was noted to reverse the effectiveness of the agonist-induced hypoestrogesism in decreasing nonmyoma volume, i.e., the treatment prevented the beneficial effects of the agonist treatment. When used in an add-back regimen, the progestin reduced hot flashes and urinary calcium loss but there was also a modest increase in total uterine volume, although not back to baseline values. See, Case et al, *J. Clin. Endocrinol. Metab.*, 76:1217, 1993.

It has now been discovered that a regimen of gonadotropin releasing hormone analog combined with an antiprogestin will act to alleviate the symptoms of ovarian estrogen dependent conditions such as of endometriosis, uterine leiomyomata, PMS and DUB and additionally will ameliorate the bone loss effects due to estrogen depletion by GnRH analog administration. It is accordingly, the object of this invention, to provide such a regimen. This and other objects of the invention will become apparent to those of ordinary skill in this art from the following detailed description.

BRIEF DESCRIPTION OF THE DRAWINGS

FIG. 3 is a graph of bone mineral density as a result of various treatment regiments.

SUMMARY OF THE INVENTION

Figure 1:
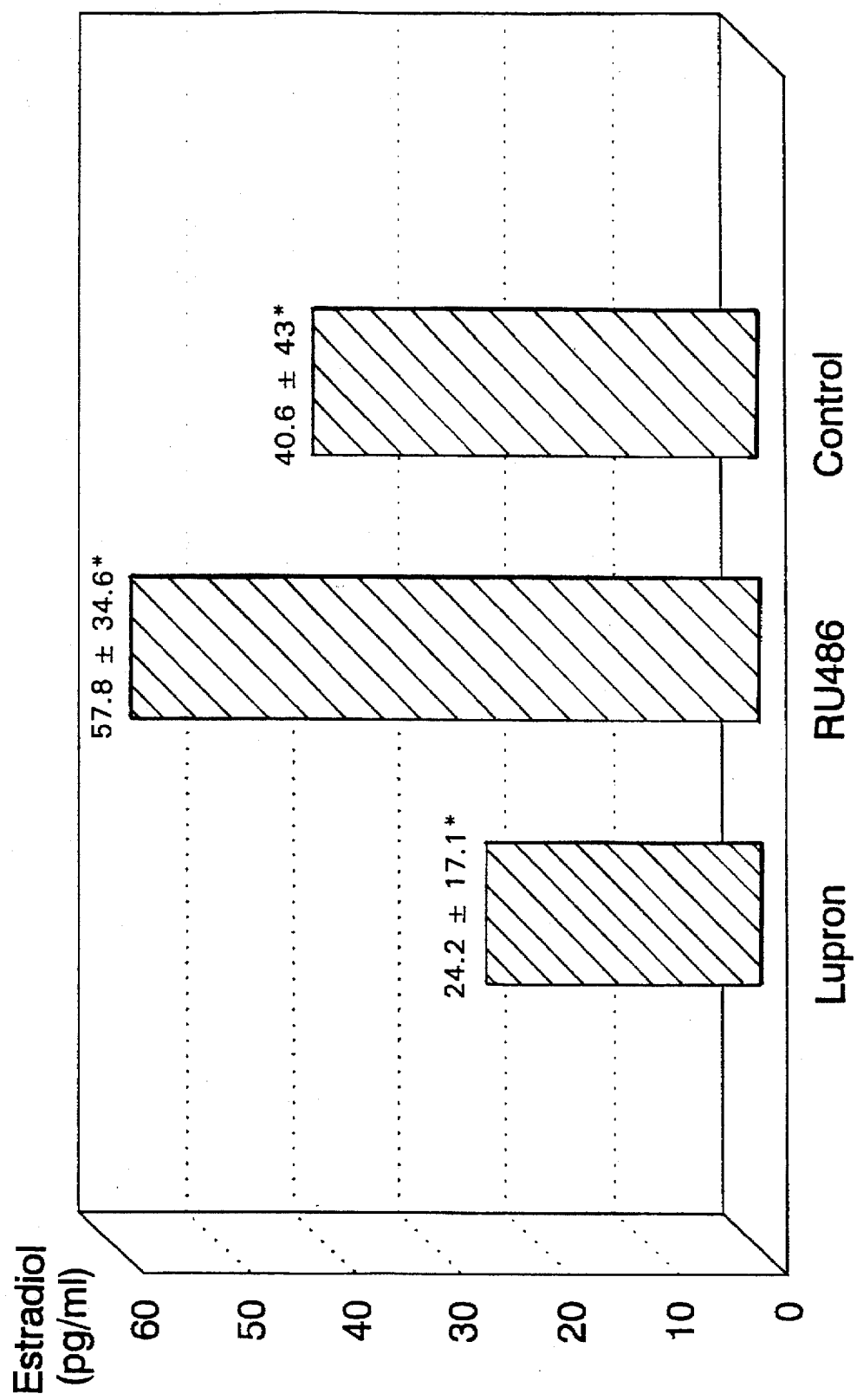
FIG. 1 is a graph of mean daily serum estradiol.

This invention broadly relates to the treatment of ovarian estrogen dependent conditions such as endometriosis, myoma tumors (e.g., uterine leiomyomata), PMS and/or DUB. More particularly, it relates to a method of treating an ovarian estrogen dependent condition by administering a gonadotropin releasing hormone analog for a period of time of at least about 30 days which is sufficient to lower the circulating serum estrogen level to approximately 20 pg/ml or less and thereafter administering an endometrium antiproliferative and bone conserving amount of antiprogestin.

DESCRIPTION OF THE INVENTION

A woman suffering from an ovarian estrogen dependent condition such as endometriosis, uterine leiomyomata, PMS and/or DUB is treated, in accordance with the present invention, with both a gonadotropin releasing hormone analog and an antiprogestin. Surprisingly, not only are the symptoms of the endometriosis, PMS, DUB or myoma tumors, ameliorated, but also the bone density loss associated with estrogen deprivation is counteracted and in some instances is actually reversed. As a result, tolerance to the treatment regimen and the length of treatment can be increased and the utility of antiprogestin administration beyond six months is presented. Although the basal level of circulating estrogen is higher during the antiprogestin administration than during GnRH against therapy, no apparent recovery of the disease state has been noted while at the same time bone density is conserved or increased. While not being limited to theory, it is believed that there are differential thresholds of estrogen effect such that after initial reduction of estrogen, there is a window of higher concentration at which the reduced level of circulating estrogen establishes therapeutic benefit and the disease state is ameliorated, but the same concentration does not induce rapid bone loss, resulting in bone mass being conserved or increased.

Gonadotropin releasing hormone is a small polypeptide produced in the hypothalamus and is sometimes termed gonadotropic releasing hormone, lutenizing hormone releasing hormone, GnRH or LHRH. Any analog, whether an antagonist or agonist, of this polypeptide can be used in the present invention.

Examples of gonadotropin releasing hormone antagonist can be found, inter alia, in U.S. Pat. Nos. 4,409,208, 4,547,370, 4,565,804, 4,569,927 and 4,619,914, 5,198,533 and WO 89/01944, the disclosures of which are incorporated herein by reference. Examples of such antagonists include Antide (a decapeptide represented by the formula D-Ac-D-2-Nal$^1$-DpClPhe$^2$-D-3-Pal$^3$-Ser$^4$-NiLys$^5$-D-NicLys$^6$-Leu$^7$-ILys$^8$-Pro$^9$-D-Ala$^{10}$), [Ac-D4ClDPhe$^1$, D4ClDPhe$^2$, DTrp$^3$, DArg$^6$, DAla$^{10}$] GnRH, [Ac-4ClDPhe$^2$, D$_3$Pal$^3$, Arg$^5$, D$_2$Nal$^6$, DAla$^{10}$] GnRH, [Ac-D2-Nal$^1$, 4ClDPhe$^2$, DTrp$^3$, DArg$^6$, DAla$^{10}$] GnRH, [Ac-D$_2$Nal$^1$, 4FDPhe$^2$, DTrp$^3$, DArg$^6$] GnRH, [Ac-D2Nal$^1$, 4ClDPhe$^2$, DTrp$^3$, DhArg(Et$_2$)$^6$, DAla$^{10}$] GnRH, and [Ac-Nal$^1$, DME4ClPhe$^2$, DPal$^3$, Ser$^4$, Tyr$^5$, DArg$^6$, Le$^7$, ILys$^8$, Pro$^9$, DAla$^{10}$] GnRH.

Examples of gonadotropin releasing hormone agonists include leuprolide, nafarelin, buserelin, [DAla$^6$, des Gly-NH$_2$$^{10}$]GnRH, [DLys$^6$]GnRH, [DAla$^6$]GnRH, [2-Me-Ala$^6$] GnRH, [D-α-aminobutyroyl$^6$, des-GlyNH$_2$$^{10}$]GnRH triporelin, lutrelin, goserelin, histrelin and the like.

The gonadotropin releasing hormone analogs employed in the present invention can be administered in the form of pharmaceutically acceptable non-toxic salts or complexes. The salts include acid addition salts such as for instance hydrochloride, hydrobromide, sulfate, phosphate, nitrate, oxalate, fumarate, gluconate, tannate, maleate, acetate, benzoate, succinate, alginate, malate, ascorbate, tartrate and the like. The complexes can be with metals such as for example zinc, barium, calcium, magnesium, aluminum and the like.

The gonadotropin releasing hormone releasing hormone analog aspect of the present invention is similar to the previous use of such analogs for the treatment of endometriosis and/or uterine leiomyomata. Thus not only any known GnRH analog can be employed, but also the dosage amount and mode of administration heretofore employed can also be employed in the practice of the present invention. Thus, the route of administration can be any conventional route where the analog is active, for instance orally, intravenously, subcutaneously, intramuscularly, sublingually, percutaneously, rectally, intranasally or intravaginally. Similarly, the administration form can be a tablet, dragee, capsule, pill, nasal mist, aerosol, pellet, implant (or other depot) and the like.

The amount of gonadotropin releasing hormone analog administered is that sufficient to lower circulating estrogen to about 20 pg/ml or below by the end of a time period of about 1 to 6 months and is similar to that practiced heretofore. Broadly the amount can be in the range of about 0.05 to 50 mg, preferably about 0.5 to 10.0 mg daily. The determination of an effective dose is a routine exercise in the pharmaceutical arts, taking various physical parameters such as weight, age and the like into account, and is best determined by the attending clinician. The administration can be periodic, such as on a monthly basis or continuous such as on a daily basis. Daily administration is preferred because individuals are more likely to follow the treatment regimen and not to forget or overlook a periodic administration schedule. The use of a depot administration, such as the employment of leuprolide acetate commercially available under the trademark Lupron Depot, can be convenient.

The antiprogestin to be combined with GnRH agonist or GnRH antagonist can be a progesterone receptor antagonist or a pharmaceutically suitable agent that counteracts the normal biological activity of progesterone. A preferred antiprogestin is a progesterone receptor antagonist, either steroidal or non-steroidal, that manifests some capacity to diminish estrogen secretion but more importantly, blocks estrogen stimulation of the tropic tissues such as endometriosis, ectopic or in the uterus, or leiomyomata tissue. For example, RU 486 is particularly suitable in the practice of this invention.

Examples of antiprogestins which can be employed in this invention are RU 486 ("mifepristone", Roussel Uclaf, Paris; U.S. Pat. No. 4,386,085); and "onapristone" (Schering Ag, Berlin; U.S. Pat. No. 4,780,461) and the steroids described in the following patents and patent applications: U.S. Pat. No. 4,609,651, especially the compound lilopristone (11β-(4-dimethylaminophenyl)-17β-hydroxy-17α-(3-hydroxy-prop-1-(Z)-enzyl-4,9(10) estradien-3-one); U.S. application Ser. No. 06/827,050, especially the compounds 11β-(4-acetylphenyl)-17β-hydroxy-17α-(1-propinyl)-4,9-estradien-3-one and 11β-(4-acetylphenyl)-17β-hydroxy-17α-(3-hydroxy-1(2)-propenyl)-4,9-estradien-3-one; U.S. application Ser. No. 07/283,632; published European patent application EP-A 04042831; published PCT application WO 91/14704; and other anti-progestins, e.g., U.S. Pat. No. 4,891,368.

The antiprogestin can be administered by way of any art recognized means as practiced in the pharmaceutical arts. For example, a suitable antiprogestin may be so formulated so that it can be administered orally, subcutaneously, intramuscularly, buccally, via a skin patch for transdermal absorption, contained within an inert matrix which is implanted within the body and in the depot state or intravaginally in a matrix that slowly releases the antiprogestin (such an implant is taught in U.S. Pat. Nos. 4,957,119 and 5,088,505 and the like).

Pharmaceutical formulations containing the antiprogestin and a suitable carrier can be solid dosage forms which includes tablets, capsules, cachets, pellets, pills, powders or granules; topical dosage forms which includes solutions, powders, fluid emulsions, fluid suspensions, semi-solids, ointments, pastes, creams, gels or jellies and foams; and parenteral dosage forms which includes solutions, suspensions, emulsions or dry powder comprising an effective amount of antiprogestin as taught in this invention. It is known in the art that the active ingredient, the antiprogestin, can be contained in such formulations in addition to pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and other means of augmenting the medicinal entity. The means and methods for administration are known in the art and an artisan can refer to various pharmacologic references for guidance. For example, "Modern Pharmaceutics", Banker & Rhodes, Marcel Dekker, Inc. 1979; "Goodman & Gilman's The Pharmaceutical Basis of Therapeutics", 6th Edition, MacMillan Publishing Co., New York 1980 can be consulted.

In some instances, the administration of the gonadotropin releasing hormone analog and the antiprogestin may overlap. In that case, the two components can be co-administered utilizing the same or different dosage forms or means, for example the same tablet. Application of the components, compositions and the methods of this invention for the medical and/or pharmaceutical use which are described in this text can thus be accomplished by any clinical, medical or pharmaceutical methods or techniques as are presently or prospectively known to those skilled in the art.

The gonadotropin releasing hormone analog is administered for a period of time of at least 30 days which is sufficient to lower the circulating estrogen level in the blood to about 20 picograms per ml or less and preferably to lower the circulating estrogen level to at least about 10 picograms per ml or below, thereby simulating postmenopausal estrogen levels. At present, the analog administration is halted after about 6 months although it is possible this can be extended if a bone conserving amount of antiprogestin administration is begun in timely fashion. The preferred present length of administration of GnRH agonist is roughly three months.

The administration of the antiprogestin is commenced when the circulating estrogen level has fallen to 20 pg/ml or less, and preferably about 10 pg/ml or less. The antiprogestin administration period can overlap the gonadotropin releasing hormone analog administration period or can commence on cession of GnRH analog administration or there can be a gap between administration intervals as long as the circulating estrogen level does not remain above about 20 pg/ml. The amount of antiprogestin is that which both inhibits estrogenic endometrial proliferation, i.e. an anti-proliferation effective amount, and also is a bone conserving effective amount. In this connection, bone conserving means that the bone mass (density) is either maintained or increased. In the case of the antiprogestin RU 486, this is generally about 0.05 to 10.0 mg/kg, and preferably about 0.5 to 5.0 mg/kg daily. Other milligram amounts may be appropriate in the case of different anti-progestins. Regimens in which the dosage of the anti-progestin (and the GnRH analog) is periodically varied is also within the scope of this invention. Also, while an anti-proliferative effective amount of the antiprogestin is administered, a minor amount of periodic bleeding or spotting on a monthly or yearly basis can occur. In other words, the amenorrhea state (absence of menstrual like bleeding) established in this invention is substantially, but not necessarily totally, complete. The amount of antiprogestin employed can, as with the gonadotropin releasing hormone analog, be determined by using art recognized methods such as for instance by establishing dose-response curves in suitable primate models having an inherent ovarian menstrual cycle similar to that of women and extrapolating to humans, extrapolating from suitable in vitro systems or determining effectiveness in clinical trials. The attending clinician will taken weight, age and other physical and medical parameters into account when establishing an appropriate dosage amount.

In order to further illustrate the present invention, specific examples are set forth below. It will be appreciated, however, that these examples are illustrative only and are not intended to limit the scope of the invention.

EXAMPLE 1

For the purposes of this study, the gonadotropin releasing hormone agonist selected was leuprolide acetate, the antiprogestin selected was RU 486 and these were administered to female cynomolgus monkeys, which are recognized to be a highly desirable model for human research.

Thirty-six adult female cynomolgus monkeys (*Macaca facularis*) having regular menstrual cycles were housed in individual cages which had food and water available ad librium.

Using anesthesia (ketamine 20 mg/kg im, xylazine, 1 mg/kg) on day 3 of the menstrual cycle, a diagnostic laparoscopy was performed to rule out pelvic adhesive disease or extant endometriosis. Monkeys with observable pelvic adhesions were excluded. Blood was collected on menstrual days 8–14 via venipuncture (ketamine 10 mg/kg im), and serum assayed for estradiol-17β by RIA. Laparotomy (ketamine 20 mg/kg, xylazine 1 mg/kg) was performed 3–5 days after a clearly defined pre-ovulatory estradiol peak. A 2 cm fundal hysterotomy was performed and approximately 100 mg of endometrium removed by curettage and minced in sterile 0.9% saline. The uterine incision was closed with 4-0 vicryl suture. The minced endometrial tissue was injected sub-peritoneally into five sites, namely, the left and right vesicouterine fold, right and left broad ligaments, and the cul-de-sac.

During the subsequent menstrual cycle, laparotomy was performed 3 to 5 days after the mid-cycle estradiol surge. The presence of ectopic endometrial tissue and the extent of adhesions were noted, with peritoneal implants carefully measured. Photographs of all lesions were taken and assigned a random number for later histological staging of the endometriosis by an independent observer. Biopsies were taken from representative lesions, and the tissue fixed in 10% formalin for histologic examination after hematoxylin and eosin staining.

Primates were divided equally into four treatment groups (N=8). Group 1 was given monthly injections of the gonadotropin releasing hormone agonist, in an amount of 80 µg/kg im on menstrual day 21 of the second laparotomy cycle. This was continued at 28 day intervals for a total of 3 injections, at which time weekly injections of the antiprogestin RU 486 began, (5 mg/kg im, in oil, initially, then 2 mg/kg/week). RU 486 was continued for a period of 24 weeks.

Group 2 was given weekly im injections of RU 486 alone (5 mg/kg initially, then 2 mg/kg/week) beginning on menstrual day 1 of the cycle after the endometriosis was confirmed. This was continued for a treatment period of 36 weeks. Group 3 was given doses of the GnRH analog alone for 36 weeks. Group 4 was a control and received vehicle, 0.5 ml of normal saline im, weekly for 36 weeks.

After daily injections began, a staging laparotomy was performed every 12 weeks until the end of therapy to assess the progression or regression of the disease.

Using ketamine anesthesia, blood was collected on alternate days in all groups for 28 days after the initial treatments following confirmation of active endometriosis. The serum was frozen for later analysis. Thereafter, blood was collected weekly. Blood draws continued until spontaneous menses resumed, or two months after the conclusion of injections, whichever came first. Serum was frozen, labelled, and stored for subsequent radioimmunoassay. Estradiol and progesterone were assayed using RIA (ICN Biomedical, Los Angeles, Calif.).

Vaginal epithelium was obtained at the time of each surgery using Kevorkian biopsy forceps taken from the lateral vaginal side of the upper two-thirds of the vagina.

The monkeys were examined daily on morning rounds. Changes in behavior were noted. Skin was examined for signs of rash or inflammatory changes at the injection site. The perineum was examined for signs of menses. Body weight was determined monthly, and changes in appetite noted.

The Dual X-ray Absorptiometry bone density determinations were:

| GROUP | PRE-TREATMENT (MEAN ± SD) | AFTER 3 MONTHS | AFTER 6 MONTHS |
|---|---|---|---|
| ANALOG/ANTI-PROGESTIN | 0.481 ± .046 | 0.481 ± .056 | 0.049 ± .046 |
| ANTIPROGESTIN | 0.501 ± 0.029 | 0.541 ± 0.033* | NA |
| CONTROL | 0.441 ± 0.028 | 0.446 ± 0.047 | NA |

*Paired t-test, p = 0.08 versus pretreatment density

Urine was collected at the time of blood sampling. The first sample was taken at the time of the first laparotomy and the second sample was taken at the time of the first injection with subsequent samples drawn every four weeks from the time of the second urine sample. Dual X-ray absorptiometry (DXA, Norland) was used to measure the bone mineral density of the lumbar spine. Primates were anesthetized with ketamine and restrained to minimize motion artifact. DXA was performed before injections began and at three month intervals until completion of the study.

At the time of each laparotomy, a small repeat hysterotomy was performed for the purpose of endometrial sampling for histologic examination.

It was observed that both the antiprogestin or GnRH analog treatments alone resulted in suppression of ovulation. There was only one documented ovulation per 24 months (progesterone >3 ng/ml) in each of treatment groups 1–3 versus 18 apparent ovulations per 24 months in the control group 4 (vehicle only). The mean tonic serum estradiol levels varied between the groups as shown in FIG. 1. The GnRH analog-treated group was rather more uniformly suppressed (24.2 ±17 pg/ml) whereas among the control group estrogen levels varied rather widely (40.6±43 pg/ml) as expected. Interestingly, the RU 486 treatment group had a higher mean estradiol level in circulation than either of the other groups (57.8±34.6, Kruskall-Wallis, p<0.05).

Figure 2:
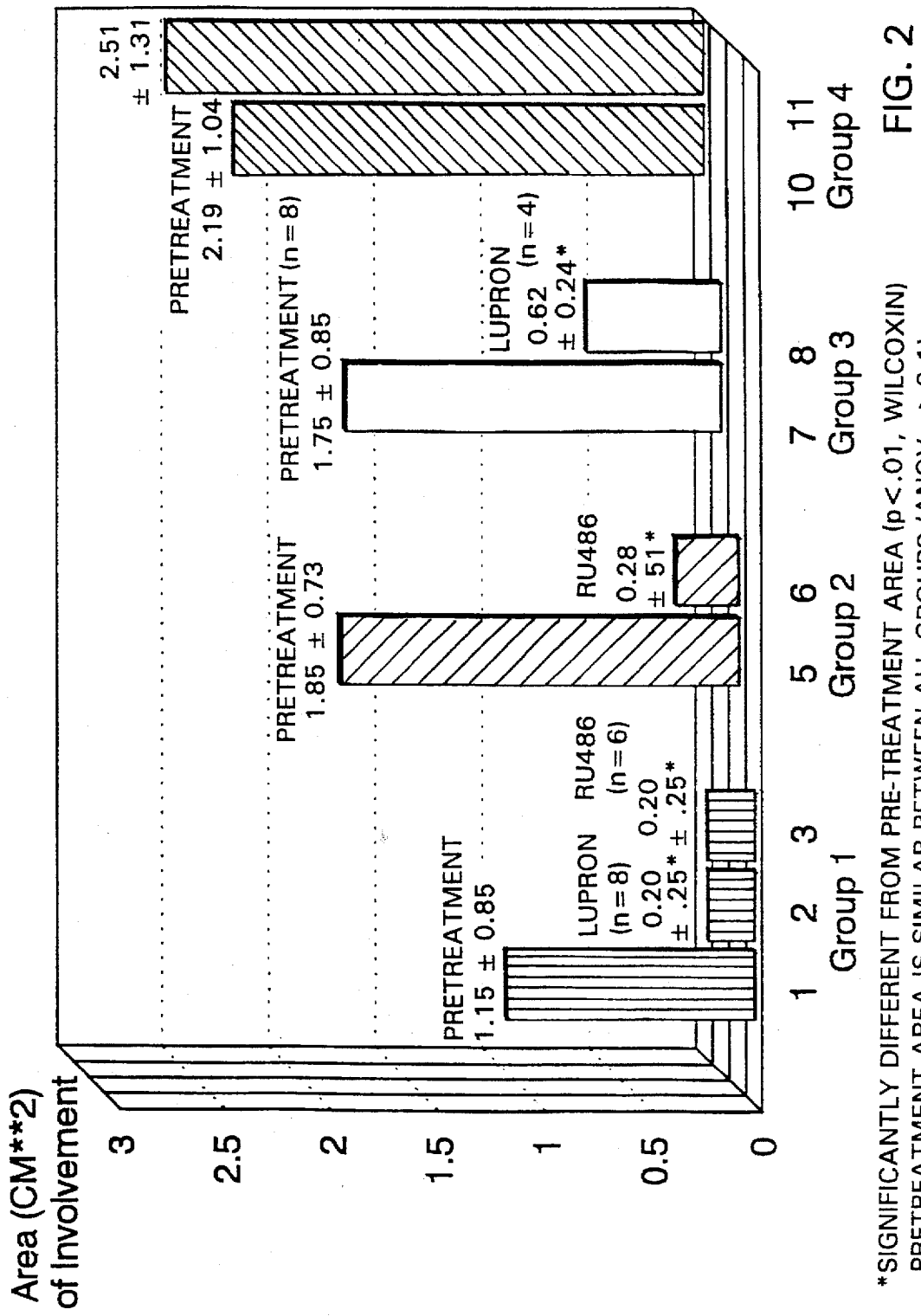
FIG. 2 is a graph of perionateal endometriosis resulting from various treatment regiments.

The area of ectopic endometrium visualized on peritoneal surfaces is shown in FIG. 2. The pre-treatment areas for all groups were similar (ANOVA, p>0.1). The post-treatment area was significantly different from pre-treatment areas for groups 1, 2 and 3, and from the post-treatment area in the control, group 4 (Wilcoxon, p<0.05). This observation shows that both GnRH analog and antiprogestin had an unequivocal limiting impact on the size of the endometrial implants. In Group 1 where the primates were switched to RU 486 for three months after completing the course of GnRH analog therapy, the mean area of peritoneal disease remained the unchanged.

There was no change in bone density after three months of GnRH alone only or vehicle control. This was expected since statistically bone loss in a population does not become apparent until sometime between 3 and 6 months. Three animals in group 1 lost bone density after 3 months of GnRH analog treatment while the others remained unchanged or increased. An example of a fast bone loser in monkey 2190 and the data with respect to this working is shown in FIG. 3. A significant degree of bone loss after the three month GnRH analog treatment is apparent. The antiprogestin treatment counteracted this loss and there was a marginally significant increase in bone density (paired t-test, p=0.08) after 3 months of antiprogestin treatment.

Daily assessment of well-being revealed little in the way of behavioral changes, inflammatory skin changes or alterations in dietary habits. Weights determined at monthly intervals showed no significant changes in any of the groups.

The histological assessments of endometrial and vaginal epithelium by hematoxylin and eosin staining are summarized as follows:

| GROUP | ENDOMETRIUM MENTRUAL PHASE | THICKNESS | VAGINAL EPITHELIUM AND KERATIN |
|---|---|---|---|
| ANALOG ONLY | INACTIVE EARLY PROLIFERATIVE | THIN | THIN |
| ANALOG/ ANTIPROGESTIN | INTERVAL PHASE, STATIC | MODERATELY THIN | MODERATELY THICK |
| CONTROL | CYCLIC | MODERATELY THICK, VARIABLE | CYCLIC |

The GnRH analog exposed endometrium was uniformly thin and weakly proliferative. The antiprogestin exposed endometrium was thinner than in control monkeys, but consistently appeared to be interval phase, such as day 17 in a typical normal menstrual cycle. Control treatment primates had cycling endometrium, thicker on all biopsy days than either of the other groups. The thickness of the vaginal epithelium, the keratin layer, and to the base of the rete pegs, were both greater in the antiprogestin group than in the GnRH analog groups. The findings in the control group were variable, but the keratin layer was thicker than after GnRH analog treatment.

Ectopic endometriotic lesions, like in situ endometrium, undergo gradual regression during three months of therapy with endometrial changes occurring more rapidly during gonadotropin releasing hormone analog treatment than with antiprogestin alone. The above results demonstrate that the antiprogestin was able to sustain the reduced surface of peritoneal endometriosis after discontinuing the analog treatment period. Endometriosis in the control primates did not improve spontaneously and indeed, the endometriotic lesions worsened progressively over three months.

Three of the primates used in the study were identified as those which lose bone mineral rapidly after medically induce hypoestrogenism via GnRH analog therapy. It was demonstrated that bone density returned to baseline after three months of antiprogestin administration. As a generalization, the antiprogestin treated primates had a marginally significant increase in bone density from their baseline measurement. Vaginal atrophy, a problem with gonadotropin releasing hormone analogs, was not noted. The thickness of the vaginal epithelium and keratin layer was thicker in the antiprogestin treatment group, a condition which usually translates into easier maintenance of intercourse, diminished urinary incontinence and decreased dysuria. In addition to these advantages in bone and vaginal epithelium, the endometrium remained moderately thin when compared to untreated cycling control monkeys and this is attributed to the antiproliferative action of the antiprogestin.

EXAMPLES 2–10

The regimen described in Example 1 is repeated with the following combinations of agents:

| Example | Analog | Antiprogestin |
|---------|--------|---------------|
| 2 | nafarelin | onapristone |
| 3 | buserelin | lilopristone |
| 4 | antide | 11β-(4-acetyl-phenyl)-17β-hydroxy-17α-(1-propinyl)-4,9-estradien-3-one |
| 5 | goserelin | 11β-(4-acetyl-phenyl)-17β-hydroxy-17α-3-hydroxy-1(2)-propenyl)-4,9-estradien-3-one |
| 6 | histrelin | mifepristone |
| 7 | lutrelin | onapristone |
| 8 | tristorelin | lilopristone |
| 9 | Nal—Glu | mifepristene |
| 10 | Azaline B | mifepristone |

Various changes and modifications can be made in the present invention without departing from the spirit and scope thereof. The various embodiments which have been described and illustrated herein were intended to be representative and not limiting.

What is claimed is:

1. A method of treating an ovarian estrogen dependent condition which comprises administering gonadotropin releasing hormone analog to a women for a period of time of at least about 30 days which is sufficient to lower the circulating estrogen level in the blood to about 20 pg/ml or less and after said about thirty days administering an antiproliferative and bone conserving amount of antiprogestin, wherein said analog is a gonatropin releasing hormone agonist or antagonist.

2. The method of claim 1, in which the analog and antiprogestin administration is less frequent than daily.

3. The method of claim 1, in which the analog and antiprogestin administration is daily.

4. The method of claim 1, in which the administration of the analog and the antiprogestin overlap.

5. The method of claim 1, in which the administration of the analog and the antiprogestin do not overlap.

6. The method of claim 1, in which the analog is administered for up to about six months.

7. The method of claim 1, in which the analog is a gonadotropin releasing hormone agonist.

8. The method of claim 1, in which the analog is a gonadotropin releasing hormone antagonist.

9. The method of claim 1, in which the gonadotropin releasing hormone analog is administered for a period of time sufficient to lower the circulating estrogen level to about 10 pg/ml or less.

10. The method of claim 1, in which the antiprogestin is a progestin receptor antagonist.

11. The method of claim 10, in which the antiprogestin is mifepristone.

12. The method of claim 1, in which the amount of antiprogestin is sufficient to effect a state of amenorrhea in said woman.

13. The method of claim 1 in which the ovarian estrogen dependent condition is endometriosis.

14. The method of claim 1 in which the ovarian estrogen dependent condition is uterine leiomyomata.

15. The method of claim 1 in which the ovarian estrogen dependent condition is PMS.

16. The method of claim 1 in which the ovarian estrogen dependent condition is DUB.

* * * * *